United States Patent [19]

Eidenschink et al.

[11] Patent Number: 4,713,197
[45] Date of Patent: Dec. 15, 1987

[54] NITROGEN-CONTAINING HETEROCYCLIC COMPOUNDS

[75] Inventors: Rudolf Eidenschink, Münster; Joachim Krause, Dieburg; Reinhard Hittich, Modautal; Eike Poetsch, Mühltal; Bernhard Scheuble, Alsbach; Georg Weber, Erzhausen; Ludwig Pohl, Darmstadt, all of Fed. Rep. of Germany

[73] Assignee: Merck Patent Gesellschaft mit beschrankter Haftung, Darmstadt, Fed. Rep. of Germany

[21] Appl. No.: 692,097

[22] Filed: Jan. 17, 1985

[30] Foreign Application Priority Data

Jan. 17, 1984 [DE] Fed. Rep. of Germany ....... 3401321

[51] Int. Cl.$^4$ ................. C09K 19/34; C07D 239/26; C07D 239/34; C07D 237/08; C07D 237/14; C07D 241/12; C07D 241/18; C07D 403/06; C07D 403/12; C07D 403/14; C07D 405/06; C07D 405/12; C07D 405/14; C07D 339/08; C07D 319/06

[52] U.S. Cl. ................ 252/299.61; 252/299.5; 350/350 R; 544/238; 544/239; 544/240; 544/241; 544/224; 544/295; 544/296; 544/315; 544/318; 544/242; 544/333; 544/334; 544/335; 544/336; 544/406; 544/408; 544/409; 544/410

[58] Field of Search ............ 252/299.61, 299.5; 350/350 R; 544/238-241, 224, 295, 296, 315, 318, 333-335, 242, 406, 408, 409, 410, 336

[56] References Cited

U.S. PATENT DOCUMENTS

| | | | |
|---|---|---|---|
| 4,062,798 | 12/1977 | Boller et al. | 252/299.61 |
| 4,273,929 | 6/1981 | Boller et al. | 252/299.61 |
| 4,311,610 | 1/1982 | Zaschke et al. | 252/299.61 |
| 4,358,393 | 11/1982 | Zaschke et al. | 252/299.63 |
| 4,438,268 | 3/1984 | Zaschke et al. | 252/299.62 |
| 4,452,718 | 6/1984 | Schadt et al. | 252/299.5 |
| 4,510,069 | 4/1985 | Eidenschink et al. | 252/299.5 |
| 4,512,636 | 4/1985 | Andrews et al. | 252/299.61 |
| 4,526,704 | 7/1985 | Petrzilka et al. | 252/299.61 |
| 4,528,114 | 7/1985 | Petrzilka | 252/299.61 |
| 4,533,488 | 8/1985 | Fukui et al. | 252/299.61 |
| 4,564,694 | 1/1986 | Hirai et al. | 252/299.61 |
| 4,565,425 | 1/1986 | Petrzilka et al. | 252/299.61 |
| 4,581,155 | 4/1986 | Goto et al. | 252/299.5 |
| 4,609,485 | 9/1986 | Kitano et al. | 252/299.61 |
| 4,623,477 | 11/1986 | Ogawa et al. | 252/299.61 |
| 4,632,515 | 12/1986 | Gray et al. | 252/299.61 |
| 4,659,502 | 4/1987 | Fearon et al. | 252/299.61 |

FOREIGN PATENT DOCUMENTS

| | | | |
|---|---|---|---|
| 84194 | 7/1983 | European Pat. Off. | 252/299.63 |
| 111695 | 6/1984 | European Pat. Off. | 252/299.61 |
| 149208 | 7/1985 | European Pat. Off. | |
| 152697 | 8/1985 | European Pat. Off. | 252/299.61 |
| 3315295 | 10/1984 | Fed. Rep. of Germany | 252/299.61 |
| 3322982 | 1/1985 | Fed. Rep. of Germany | 252/299.61 |
| 3404116 | 8/1985 | Fed. Rep. of Germany | 252/299.61 |
| 3405914 | 8/1985 | Fed. Rep. of Germany | 252/299.61 |
| 145913 | 1/1981 | German Democratic Rep. | 252/299.61 |
| 54-11887 | 1/1979 | Japan | 252/299.61 |
| 54-41285 | 4/1979 | Japan | 252/299.61 |
| 59-39876 | 3/1984 | Japan | 252/299.61 |
| 59-98065 | 6/1984 | Japan | 252/299.61 |
| 60-78972 | 5/1985 | Japan | 252/299.61 |
| 60-109569 | 6/1985 | Japan | 252/299.61 |
| 60-172971 | 9/1985 | Japan | 252/299.61 |
| 60-193969 | 10/1985 | Japan | 252/299.61 |
| WO86/00067 | 1/1986 | PCT Int'l Appl. | 252/299.61 |
| 2092169 | 8/1982 | United Kingdom | 252/299.61 |

OTHER PUBLICATIONS

Green, D. C., et al., IBM Tech. Discl. Bull., vol. 15, No. 8, pp. 2467–2468, (1/1973).

Schubert, H., Wiss. Z. Univ. Halle, XIX'70 M, H.5, S 1–18.

Primary Examiner—Teddy S. Gron
Attorney, Agent, or Firm—Millen & White

[57] ABSTRACT

Nitrogen-containing heterocyclic compounds of the formula I $$R^1-(A-Z)_n-A-R^2 \qquad I$$

wherein $R^1$ and $R^2$ in each case independently of one another are alkyl group with 1–15 C atoms, wherein one or two non-adjacent $CH_2$ groups can also be replaced by 0 atoms and/or —CO— group and/or —O—CO— groups and/or —CO—O— groups, and one of the radicals $R^1$ and $R^2$ can also be H, CN, F, Cl or Br, the groups A in each case independently of one another are a 1,4-phenylene group, wherein one or two CH groups can also be replaced by N atoms, a 1,4-cyclohexylene group, wherein one or two $CH_2$ groups which are not adjacent can be replaced by 0 atoms, a 1,3-dithiane-2,5-diyl group, a 1,4-bicyclo(2,2,2)-octylene group, a decahydronapthalene-2,6-diyl group or a 1,2,3,4-tetrahydronaphthalene-2,6-diyl group, the group Z in each case independently of one another are —CO—O—, —O—CO—, —$CH_2CH_2$—, —$OCH_2$—, —$CH_2O$— or a single bond and n is 3 or 4, with the proviso that (a) at least one of the groups A is a "1,4" phenylene group, wherein two CH groups are replaced by N atoms, and (b) at least one of the other groups A contains a cycloaliphatic radical and/or at least one group Z is not a single bond, can be used as components of liquid crystal phases.

15 Claims, No Drawings

NITROGEN-CONTAINING HETEROCYCLIC COMPOUNDS

BACKGROUND OF THE INVENTION

This invention relates to new N-containing heterocyclics.

SUMMARY OF THE INVENTION

It is an object of this invention to provide new compounds having valuable properties as liquid crystals, e.g., new stable liquid crystal or mesogenic compounds which are suitable as components of liquid crystal phases.

Upon further study of the specification and appended claims, further objects and advantages of this invention will become apparent to those skilled in the art.

These objects have been attained by providing nitrogen-containing heterocyclic compounds of the formula I

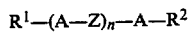  I wherein $R^1$ and $R^2$ in each case independently of one another are an alkyl group with 1–15C atoms, wherein one or two non-adjacent $CH_2$ groups can also be replaced by O atoms and/or —CO— groups and/or —O—CO— groups and/or —CO—O— groups, and one of the radicals $R^1$ and $R^2$ can also be H, CN, F, Cl or Br, the groups A in each case independently of one another are a 1,4-phenylene group, wherein one or two CH groups can also be replaced by N atoms, a 1,4-cyclohexylene group, wherein one or two $CH_2$ groups which are not adjacent can be replaced by O atoms, a 1,3-dithiane-2,5-diyl group, a 1,4-bicyclo(2,2,2)-octylene group, a decahydronapthalene-2,6-diyl group or a 1,2,3,4-tetrahydronaphthalene-2,6-diyl group, the groups Z in each case independently of one another are —CO—O—, —O—CO—, —$CH_2CH_2$—, —$OCH_2$, —$CH_2O$— or a single bond and n is 3 or 4, with the proviso that (a) at least one of the groups A is a "1,4" phenylene group, wherein two CH groups are replaced by N atoms, and (b) at least one of the other groups A contains a cycloaliphatic radical and/or at least one group Z is not a single bond.

For simplicity, in the following text Cy is a 1,4-cyclohexylene group, Dio is a 1,3-dioxane-2,5-diyl group, Dit is a 1,3-dithian-2,5-diyl group, Bi is a 1,4-bicyclo(2,2,2)-octylene group, Phe is a 1,4-phenylene group, Pyr is a pyrimidine-2,5-diyl group and Pyn is a pyridazine-3,6-diyl group.

DETAILED DISCUSSION

Similar compounds are mentioned, for example, in Japanese Preliminary Published Application 54-041,285. However, in contrast to the present compounds, the compounds mentioned therein contain no cycloaliphatic rings (Cy, Dio, Dit, or Bi) or no bridge member Z.

Like similar compounds, the compounds of the formula I can be used as components of liquid crystal phases, especially for displays based on the principle of the twisted cell (TN displays), the guest/host effect, the effect of deformation of orientated phases or the effect of dynamic scattering.

It has been found that the compounds of the formula I are outstandingly suitable as components of liquid crystal phases. In particular, stable liquid crystal phases for TN displays with high multiplex rates can be prepared with the aid of these compounds.

Surprisingly, when compounds of the formula I were added to liquid crystal phases, it was found that even relatively large additions (for example of 30%) only insignificantly increase the threshold voltage. At the same time, a considerable improvement in the steepness of the characteristic curve of the mixture occurs completely unexpectedly, so that compounds of type I are to be regarded as particularly advantageously suitable substances for the preparation of liquid crystal mixtures with a steep characteric curve. They thus allow the development of highly multiplexable mixtures of very low optical anisotropy, with which a rotating cell, in particular, can be operated in the first transmission minimum according to Gooch-Tarry. This results in a very low dependency of the contrast on the observation angle.

In addition, the range of liquid crystal substances which are suitable, from various technological viewpoints, for the preparation of nematic mixtures is quite generally considerably increased by providing the compounds of the formula I.

The compounds of the formula I have a wide range of applications. Depending on the choice of the constituents, these compounds can be used as base materials from which liquid crystal dielectrics are predominantly composed; however, compounds of the formula I can also be added to liquid crystal base materials from other classes of compounds, for example in order to reduce the dielectric and or optical anisotropy of such a dielectric. The compounds of the formula I are furthermore suitable as intermediates for the preparation of other substances which can be used as constituents of liquid crystal dielectrics.

The compounds of the formula I are colorless in the pure state and form liquid crystal mesophases in a temperature range which is preferably located for electro-optical use. They are very stable towards chemicals, heat and light.

The invention thus relates to the compounds of the formula I and to a process for their preparation, characterized in that a compound which otherwise corresponds to the formula I that contains one or more reducible groups and/or C—C bonds instead of H atoms is treated with a reducing agent, or in that a compound which otherwise corresponds to the formula I that contains one or more oxidizable groups, such as —$CH_2CH_2$—, instead of C=C-double bonds is treated with an oxidizing agent, or in that, to prepare esters of the formula I (wherein $R^1$ and/or $R^2$ are an alkyl group, wherein one or two $CH_2$ groups are replaced by —O—CO— groups and/or —CO—O groups and/or wherein at least one of the groups Z is —CO—O— or —O—CO—), a corresponding carboxylic acid or one of its reactive derivatives is reacted with a corresponding alcohol or one of its reactive derivatives, or in that, to prepare 1,3-dioxane derivatives or 1,3-dithiane derivatives of the formula I (wherein $A^1$ is 1,3-dioxane-2,5-diyl or 1,3-dithiane-2,5-diyl), a corresponding aldehyde is reacted with a corresponding diol or dithiol, or in that, to prepare ethers of the formula I (wherein $R^1$ and/or $R^2$ are an alkyl group, wherein one or two $CH_2$ groups are replaced by O atoms and/or Z is an —$OCH_2$— or —$CH_2O$—group), a corresponding hydroxy compound is etherified, and/or in that, if appropriate, a base of the formula I is converted into one of its acid addition salts by treatment with an acid, or in that, if appropriate, a compound of the formula I is liberated from one of its acid addition salts by treatment with a base.

The invention relates to the use of the compounds of the formula I as components of liquid crystal phases. The invention moreover relates to liquid crystal phases containing at least one compound of the formula I and liquid crystal display elements, in particular electrooptical display elements, containing such phases.

$R^1$, $R^2$, A and Z above and below have the meaning given, unless expressly indicated otherwise.

The compounds of the formula I accordingly include preferred compounds of the part formulae Ia in In (without a bridge member Z). For simplicity, $A^1$ below is a 1,4-phenylene group, wherein two CH groups are replaced by N atoms, $A^2$ below is a cycloaliphatic group A and p below is 2 or 3.

$R^1—A^1—(A)_p—A^2—R^2$      Ia $R^1—A^1—(A)_{p-1}—A^2—A—R^2$      Ib $R^1—A^1—(A)_{p-2}—A^2—A—A—R^2$      Ic $R^1—A^1—A^2—A—A—R^2$      Id $R^1—A^1—A^2—A—A—A—R^2$      Ie $R^1—A—A^1—(A)_{p-1}—A^2—R^2$      If $R^1—A^2—A^1—(A)_p—R^2$      Ig $R^1—A—A^1—(A)_{p-2}—A^2—A—R^2$      Ih $R^1—A—A^1—A^2—(A)_{p-1}—R^2$      Ii $R^1—A—A—A^1—(A)_{p-2}—A^2—R^2$      Ij $R^1—A—A—A^1—A^2—R^2$      Ik $R^1—A—A—A^1—A^2—A—R^2$      Il $R^1—A^2—A—A^1—(A)_{p-1}—R^2$      Im $R^1—A—A^2—A^1—(A)_{p-1}—R^2$      In

Of these, those of part formulae Ia–Ih are particularly preferred.

The compounds of the formula I furthermore include preferred compounds of the part formulae Io to Iz with a bridge member Z.

$R^1—A^1—Z—(A)_{p+1}—R^2$      Io $R^1—A^1—A—Z—(A)_p—R^2$      Ip $R^1—A^1—A—A—Z—(A)_{p-1}—R^2$      Iq $R^1—A^1—A—A—A—Z—(A)_{p-2}—R^2$      Ir $R^1—A—Z—A^1—(A)_p—R^2$      Is $R^1—A—A^1—Z—(A)_p—R^2$      It $R^1—A—A^1—A—Z—(A)_{p-1}—R^2$      Iu $R^1—A—A^1—A—A—Z—(A)_{p-2}—R^2$      Iv $R^1—A—Z—A—A^1—(A)_{p-1}—R^2$      Iw $R^1—A—A—Z—A^1—(A)_{p-1}—R^2$      Ix $R^1—A—A—A^1—Z—(A)_{p-1}—R^2$      Iy $R^1—A—A—A^1—A—Z—(A)_{p-2}—R^2$      Iz

Of these, those of part formulae Io–Iu are particularly preferred. Preferred compounds of part formula It are those of part formula It1:

$R^1—Phe—Pyr—COO—A—A—R^2$      It1

The compounds of the formula I furthermore include compounds of the part formulae I1 to I5 (with 2 bridge members Z), I6 and I7 (with 3 bridge members Z) and I8 (with 4 bridge members Z).

$R^1—A—Z—A—Z—(A)_{n-1}—R^2$      I1

$R^1—A—Z—A—A—Z—(A)_{n-2}—R^2$      I2

$R^1—A—Z—A—A—A—Z—(A)_{n-3}—R^2$      I3

$R^1—A—A—Z—A—Z—(A)_{n-2}—R^2$      I4

$R^1—A—A—Z—A—A—Z—(A)_{n-3}—R^2$      I5

$R^1—A—Z—A—Z—A—Z—(A)_{n-2}—R^2$      I6

$R^1—A—Z—A—Z—A—A—Z—A—R^2$      I7

$R^1—A—Z—A—Z—A—Z—A—Z—A—R^2$      I8

Of these, those of part formulae I1 and I2 are particularly preferred.

In the compounds of the formulae above and below, $R^1$ and $R^2$ are preferably alkyl, alkoxy or another oxaalkyl group. Compounds of the formulae above and below wherein one of the radicals $R^1$ and $R^2$ is alkyl and the other radical is alkoxy or CN are furthermore particularly preferred. Compounds of the formulae above and below wherein neither of the radicals $R^1$ and $R^2$ is H, and compounds of the formulae above and below wherein both radicals $R^1$ and $R^2$ in each case independently of one another are n-alkyl are also preferred.

The groups A are preferably Cy, Phe, $A^1$ or $A^2$ and Dio or Dit; the compound of the formula I preferably contains not more than one of the radicals Dio or Dit. particularly preferably Pyr.

The cycloaliphatic radical $A^2$ is preferably Cy, Dio, Dit or Bi, particularly preferably Cy or Dio. Preferred compounds of the formula I contain one or two, in particular two, groups $A^2$.

Z is preferably a single bond, or, secondly, preferably —CO—O—, —O—CO— or —CH$_2$CH$_2$—.

n is preferably 3.

If $R^1$ and/or $R^2$ are alkyl radicals in which one ("alkoxy" or "oxaalkyl") or two ("alkoxyalkoxy" or "dioxaalkyl") CH$_2$ groups can also be replaced by O atoms, they can be straight-chain or branched. Preferably, they are straight-chain and have 2,3,4,5,6,7,8,9,10,11 or 12 C atoms, and accordingly preferably denote ethyl, propyl, butyl, pentyl, hexyl, heptyl, octyl, nonyl, decyl, undecyl, dodecyl, ethoxy, propoxy, butoxy, pentoxy, hexoxy, heptoxy, octoxy, nonoxy, decoxy, undecoxy, dodecoxy, 2-oxapropyl (=methoxymethyl),2-(=ethoxymethyl) or 3-oxabutyl (=2-methoxyethyl), 2-, 3- or 4-oxapentyl, 2-, 3-, 4- or 5-oxahexyl), 2-, 3-, 4-, 5- or 6-oxaheptyl, and furthermore methyl, methoxy, tridecyl, tridecoxy, tetradecyl, tetradecoxy, pentadecyl, pentadecoxy, 2-, 3-, 4-, 5-, 6- or 7-oxaoctyl, 2-, 3-, 4-, 5-, 6-, 7- or 8 oxanonyl, 2-, 3-, 4-, 5-, 6-, 7-, 8- or 9-oxadecyl, 1,3-dioxabutyl (=methoxymethoxy), 1,3-, 1,4- or 2,4- dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl.

Compounds of the formulae I with branched end group substituents $R^1$ and/or $R^2$ can occasionally be of significance because of a better solubility in the usual liquid crystal base materials, but in particular as chiral doping substances, if they are optically active. Branched groups of this type overall contain not more than one chain-branching. Preferred branched radicals $R^1$ and $R^2$ are isopropyl, 2-butyl (=1-methylpropyl), isobutyl (=2-methylpropyl), 2-methylbutyl, Isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-octyloxy, 2-oxa-3-methylbutyl and 3-oxa-4-methylpentyl.

Preferred compounds of the formula I above and below are those in which at least one of the radicals contained therein has one of the preferred meanings mentioned. Particularly preferred smaller groups of compounds are those of the formulae I9 to I15:

| | |
|---|---|
| $R^1—A^1—A—A^2—A^2—R^2$ | I9 |
| $R^1—A^2—A^1—A—A^2—R^2$ | I10 |
| $R^1—A^2—A^1—A^2—A^2—R^2$ | I11 |
| $R^1—A^1—A—Z—A—A^2—R^2—$ | I12 |
| $R^1—A^1—A—Z—A^2—A^2R^2$ | I13 |
| $R^1—A^2—Z—A^1—A—Z—A—R^2$ | I14 |
| $R^1—A^2—Z—A^1—A—Z—A^2—R^2$ | I15 |

Of the compounds of the formula I, those stereoisomers in which the cycloaliphatic radicals (for example Cy, Dio, Dit) are trans-1,4-disubstituted are preferred.

Those compounds of the formula I wherein at least two of the further groups A are a cycloaliphatic radical $A^2$ and at least one group Z is —CO—O—, —O—CO— or —CH$_2$CH$_2$— are furthermore preferred.

Those of the abovementioned formulae which contain one or more of the groups Dio, Dit and/or Pyr in each case include the two possible 2,5-positionisomers.

The compounds of the formula I are prepared by methods which are known per se, such as those described in the literature (for example in the standard works, such as Houben-Weyl, Methoden der Organischen Chemie, Georg-Thieme-Verlag, Stuttgart (Methods of organic chemistry)), and in particular under reaction conditions which are known and suitable for the reaction mentioned. Variants which are known per se and are not mentioned in more detail here can also be utilized.

The expert can find corresponding synthesis methods by routine methods from the prior art (for example German Offenlegungsschrift 2,429,093; U.S. Pat. Nos. 3,826,757; 4,065,489; 4,136,053; 4,137,192; 4,130,502; 4,154,697 and 4,293,434, in respect of compounds with 1,4-cyclohexylene and 1,4-phenylene groups; U.S. Pat. No. 4,062,798, in respect of compounds with pyrimidine-2,5-diyl groups; U.S. Pat. No. 4,419,262, in respect of compounds with pyridazine-3,6-diyl groups; Japanese Published Application 58-43,961, in respect of compounds with pyrazine-2,5-diyl groups; German Offenlegungsschrift 3,227,916 and U.S. Pat. No. 4,344,856, in respect of compounds with 1,3-dioxane-2,5-diyl groups; East German Pat. No. 160,061, in respect of compounds with 1,3-dithiane-2,5-diyl groups; U.S. Pat. Nos. 4,261,652 and 4,219,256, in respect of compounds with 1,4-bicyclo(2,2,2)-octylene groups; U.S. Pat. No. 4,432,885, in respect of compounds with decahydronaphthalene-2,6-diyl groups; U.S. Pat. No. 4,386,007, in respect of compounds with 1,2,3,4-tetrahydronaphthalene-2,6-diyl groups; U.S. Pat. No. 4,439,015, in respect of compounds with —CH$_2$CH$_2$— bridge members; German Offenlegungsschriften 2,139,628, 2,535,046 and 2,800,553, in respect of compounds with Z=—CO—O— or —O—CO—; and German Offenlegungsschriften 3,001,661, 3,040,632 and 3,149,139, in respect of compounds with Z=—CH$_2$O— or —OCH$_2$—).

In general, two part compounds (for example (1) and (2) (equation 1) or (3) and (4) (equation 2)) have have condensed to give compounds of the formula I:

Equation I:

$$R^1—(A—Z)_p—M^1L^1 + L^2M^2—Z—(A—Z)_q—A—R^2$$

(1)          (2)

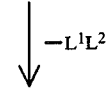

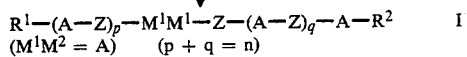

$$R^1—(A—Z)_p—M^1M^1—Z—(A—Z)_q—A—R^2 \quad I$$
$$(M^1M^2 = A) \quad (p + q = n)$$

Equation 2:

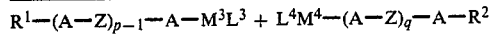

$$R^1—(A—Z)_{p-1}—A—M^3L^3 + L^4M^4—(A—Z)_q—A—R^2$$

(3)          (4)

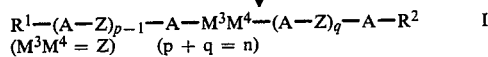

$$R^1—(A—Z)_{p-1}—A—M^3M^4—(A—Z)_q—A—R^2 \quad I$$
$$(M^3M^4 = Z) \quad (p + q = n)$$

—M$^1$L$^1$ and —M$^2$L$^2$ are units which are capable of undergoing condensation and which correspond, for example, to malonic acid derivatives (for example malondialdehyde), amidines, aldehydes, 1,3-propanediols and/or 1,3-propanedithiols. L$^1$L$^2$ are one or more groups which can be split off.

—M$^3$L$^3$ and —M$^4$L$^4$ are units which are capable of undergoing condensation, for example chosen from the group comprising —COOH, —COhalogen, —OH, —Ometal, —CH$_2$-halogen, —CH$_2$-metal, —CH$_2$—OH, —CH$_2$—O-metal, -metal, -halogen.

L$^3$ and L$^4$ are leaving groups. L$^3$L$^4$ is a group which can be split off, such as, for example, H$_2$O, H-halogen or metal-halogen.

However, corresponding intramolecular condensation reactions can furthermore also be carried out for the synthesis of compounds of the formula I (for example condensation of 1,4-diketones with hydrazine (for example German Offenlegungsschrift 3,238,350) or reaction of a butadiene derivative, for example, with acetylene dicarboxylic acid derivatives (for example Japanese Preliminary Published Application 58-144,327; Japanese Offenlegungsschrift 58-146,543).

The starting substances are known or can be obtained by methods analogous to those already known compounds. The expert can find corresponding starting substances and/or methods for their synthesis from the prior art by routine methods.

If desired, the starting substances can also be formed in situ in a manner such that they are not isolated from the reaction mixture but are immediately further reacted to give the compounds of the formula I.

Thus, the compounds of the formula I can be prepared by a process in which a compound which otherwise corresponds to the formula I that contains one or more reducible groups and/or C—C bonds instead of H atoms is reduced.

Preferred possible reducible groups are carbonyl groups, in particular ketone groups, and furthermore, for example, free or esterified hydroxyl groups or aromatically bonded halogen atoms. Preferred starting substances for the reduction correspond to the formula I, but can contain a cyclohexene ring or cyclohexanone ring instead of a cyclohexane ring, and/or a —CH=CH— group instead of a —CH$_2$CH$_2$— group, and/or a —CO— group instead of a —CH$_2$— group, and or a free or functionally modified (for example in the form of p-toluoene sulfonate) OH group instead of an H atom.

The reduction can be carried out, for example, by catalytic hydrogenation at temperatures between about 0° and about 200° and the pressures between about 1 and 200 bar, in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Catalysts which are advantageously suitable are noble metals, such as Pt or Pd, which can be used in the form of oxides (for example PtO$_2$ or PdO), on a support (for example Pd on charcoal, calcium carbonate or strontium carbonate) or in finely divided form.

Ketones can also be reduced by the methods of Clemmensen (with zinc, zinc amalgam or tin and hydrochloric acid, advantageously in an aqueous-alcoholic solution or in a heterogeneous phase system with water/toluene at temperatures between about 80° and 120°) or Wolff-Kishner (with hydrazine, advantageously in the presence of alkali, such as KOH or NaOH, in a high-boiling solvent, such as diethylene glycol or triethylene glycol, at temperatures between about 100° and 200°) to give the corresponding compounds of the formula I containing alkyl groups and/or —CH$_2$CH$_2$— bridges.

Reductions with complex hydrides are furthermore possible. For example, arylsulfonyloxy groups can be removed by reduction with LiAlH$_4$, and in particular p-toluenesulfonyloxymethyl groups can be reduced to methyl groups, advantageously in an inert solvent, such as diethyl ether or THF, at temperatures between about 0° and 100°. Double bonds can be hydrogenated (even in the presence of CN groups!) with NaBH$_4$ or tributyl-tin hydride in methanol; thus, for example, the corresponding cyclohexane derivatives are formed from 1-cyanocyclohexene derivates.

Compounds of the formula I can furthermore be obtained by a process in which a compound which otherwise corresponds to the formula I but contains one or more oxidizable groups, such as —CH$_2$—CH$_2$— groups, instead of C=C double bonds is oxidized.

Pyridazines of the formula I can be obtained, for example, by oxidizing a corresponding 4,5-dihydropyridazine or a tautomeric dihydropyridazine.

The oxidation of such a compound can be carried out in a manner which is known per se, for example with 2,3-dichloro-5,6-dicyano-p-benzoquinone in dioxane, with sodium nitrite in glacial acetic acid and ethanol, or with isopentyl nitrite in glacial acetic acid, and the like. The temperature and pressure are not critical in this reaction. However, the reaction is advantageously carried out under atmospheric pressure and at a temperature between room temperature and the reflux temperature, preferably at about room temperature. The starting compounds, however, are preferably oxidized by catalytic dehydrogenation in a manner which is known per se to give compounds of the formula I. The dehydrogenation can be carried out with any catalyst which is usually employed in dehydrogenation reactions, such as palladium, platinum and the like (if appropriate on an inert support, for example charcoal). Palladium is the preferred catalysts. Any inert organic solvent, such as alcohols, ethers, esters, carboxylic acids and the like, for example ethanol, dioxane, ethyl acetate or glacial acetic acid, can be used as the solvent. Ethanol is the preferred solvent. The temperature and pressure are not critical in this reaction. The reaction is advantageously carried out at a temperature between room temperature and the reflux temperature of the reaction mixture, under atmospheric pressure.

The 4,5-dihydropyridazines can be rearranged to give tautomeric compounds by migration of the double bonds in the dihydropyridazine ring. Such rearrangements can be triggered off, for example, by the presence of a trace of acid or base. However, since the tautomeric dihydropyridazines can also be oxidized under the above conditions to give compounds of the formula I, it is possible to react either a 4,5-dihydropyridazine or a tautomeric dihydropyridazine or a mixture of such compounds. The dihydropyridazines are accessible by reaction of corresponding 1,4-diketones with hydrazine (German Offenlegungsschrift 3,228,350).

Esters of the formula I ($R^1$ and/or $R^2$=alkyl, wherein one or two CH$_2$ groups can also be replaced by —O—CO— groups and/or —CO—O— groups or Z=—CO—O— or —O—CO—) can also be obtained by esterification of corresponding carboxylic acids (or their reactive derivative) with alcohols or phenols (or their reactive derivatives).

Particularly suitable reactive derivatives of the carboxylic acids mentioned are the acid halides, in particular the chlorides and bromides, and furthermore the anhydrides, azides or esters, in particular alkyl esters with 1-4C atoms in the alkyl group.

Reactive derivatives of the alcohols or phenols mentioned which are particularly possible are the corresponding metal alcoholates or phenolates, preferably of an alkali metal, such an Na or K.

The esterification is advantageously carried out in the presence of an inert solvent. Particularly suitable solvents are ethers, such as diethyl ethers, di-n-butyl ether, THF, dioxane or anisole, ketones, such as acetone, butanone or cyclohexanone, amides, such as dimethylformamide or phosphoric acid hexamethyltriamide, hydrocarbons, such as benzene, toluene or xylene, halogenohydrocarbons, such as carbon tetrachloride or tetrachloroethylene, and sulfoxides, such as dimethyl sulfoxide or sulfolane. Water-imiscible solvents can at the same time advantageously be used for azeotropic removal by distillation of the water and during the esterification. An excess of an organic base, for example pyridine, quinoline or triethylamine, can occasionally also be used as the solvent for the esterification. The esterification can also be carried out in the absence of a solvent, for example by simple heating of the components in the presence of sodium acetate. The reaction temperature is usually between −50° and +250°, preferably between −20° and +80°. At these temperatures, the esterification reactions are as a rule ended after 15 minutes to 48 hours.

In detail, the reaction conditions for the esterification largely depend on the nature of the starting substances used. Thus, a free carboxylic acid is as a rule reacted with a free alcohol or phenol in the presence of a strong acid, for example a mineral acid, such as hydrochloric acid or sulfuric acid. A preferred reaction procedure is the reaction of an acid anhydride or, in particular, an acid chloride with an alcohol, preferably in a basic medium, particularly important bases being alkali metal hydroxides, such as sodium hydroxide or potassium hydroxide, alkali metal carbonates or bicarbonates, such as sodium carbonates, sodium bicarbonate, potassium carbonate or potassium bicarbonate, alkali metal acetates, such as sodium acetate or potassium acetate, alkali earth metal hydroxides, such as calcium hydroxide, or organic bases, such as triethylamine, pyridine, lutidine, collidine or quinoline. In another preferred embodiment of the esterification, the alcohol or phenol is first converted into the sodium alcoholate or phenolate or potassium alcoholate or phenolate, for example by treatment with ethanolic sodium hydroxide solution or potassium hydroxide solution, this product is isolated and suspended in acetone or diethyl ether, together with sodium bicarbonate or potassium carbonate, with stirring, and a solution of the acid chloride or anhydride in diethyl ether, acetone or dimethylformamide is added to the suspension, advantageously at temperatures between about −25° and +20°.

Dioxane derivates or dithiane derivates of the formula I (wherein one of the groups A is a 1,3-dioxane-2,5-diyl group or a 1,3-dithiane-2,5-diyl group) are advantageously prepared by reacting a corresponding aldehyde with a corresponding 1,3-diol or a corresponding 1,3-dithiol (or one of its reactive derivatives), preferably in the presence of an inert solvent, such as benzene or toluene, and/or a catalyst, for example a strong acid, such as sulfuric acid or benzene or p-toluenesulfonic acid, at temperatures between about 20° and about 150°, preferably between 80° and 120°. Suitable reactive derivatives of the starting substances are, above all, acetals.

Some of the aldehydes, 1,3-diols and 1,3-dithiols mentioned and their reactive derivatives are known, and some of them can be prepared without difficulty by standard processes of organic chemistry from compounds which are known from the literature. For example, the aldehydes can be obtained by oxidation of corresponding alcohols or by reduction of corresponding carboxylic acids or their derivatives, the diols can be obtained by reduction of corresponding diesters, and the dithiols can be obtained by reaction of corresponding dihalides with NaSH.

To prepare nitriles of the formula I (wherein $R^1$ or $R^2$ is CN), the corresponding acid amides can be dehydrated. The amides can be obtained, for example, from corresponding esters or acid halides by reaction with ammonia. Examples of suitable dehydrating agents are inorganic acid chlorides, such as $SOCl_2$, $PCl_3$, $PCl_5$, $POCl_3$, $SO_2Cl_2$, $COCl_2$, and furthermore $P_2O_5$, $P_2S_5$, $AlCl_3$ (for example as the double compound with NaCl) and aromatic sulfonic acids and sulfonic acid halides. The reaction here can be carried out in the presence or absence of an inert solvent at temperatures between about 0° and 150°; examples of possible solvents are bases, such as pyridines of triethylamines, aromatic hydrocarbons, such as benzene, toluene or xylene, or amides, such as dimethylformamide.

To prepare the abovementioned nitriles of the formula I, it is also possible to react corresponding acid halides, preferably the chlorides, with sulfamide, advantageously in an inert solvent, such as tetramethylene sulfone, at temperatures between about 80° and 150°, preferably at 120°. After customary working up, the nitriles can be isolated directly.

Ethers of the formula I (wherein $R^1$ and/or $R^2$ are an alkyl group, wherein one of two $CH_2$ groups are replaced by O atoms, and/or wherein at least one Z is an $-OCH_2-$ or a $-CH_2O-$ group) can be obtained by etherification of corresponding hydroxy compounds, preferably corresponding phenols, the hydroxy compound advantageously being first converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This product can then be reacted with the corresponding alkyl halide or sulphonate or dialkyl sulfate, advantageously in an inert solvent, such as acetone, 1,2-dimethoxyethane, dimethylformamide or dimethylsulphoxide, or in an excess of aqueous or aqueous-alcoholic NaOH or KOH, at temperatures between about 20° and 100°.

A base of the formula I can be converted into the associated acid addition salt with an acid. For this reaction, it is possible to use inorganic acids, for example sulfuric acid, nitric acid, hydrogen halide acids, such as hydrochloric acid or hydrobromic acid, phosphoric acids, such as orthophosphoric acid, sulfamic acid, and furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzene sulfonic acid, p-toluene sulfonic acid, naphthalene-mono- and -di-sulfonic acids and laurylsulfonic acid. These salts are useful for regeneration of the compounds of the formula I per se.

Conversely, it is possible to liberate the base of the formula I from an acid addition salt of a compound of the formula I by treatment with a base, for example with a strong inorganic base, such as KOH or NaOH.

The liquid crystal phases according to the invention comprise 2 to 15, preferably 3 to 12, components, at least one of which is a compound of the formula I. The other constituents are preferably chosen from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis cyclohexylbenzenes, 4,4'-bis cyclohexylbiphenyls, phenyl- or cyclohexylpyrimidines, phenyl- or cyclohexyl-dioxanes, phenyl- or cyclohexyl-1,3-dithianes, 1,2-diphenylethanes, 1,2-dicyclohexylethanes, 1-phenyl-2-cyclohexyl-ethanes, optionally halogenated stilbenes, benzyl phenyl ethers, tolanes and substituted cinnamic acids.

The most important compounds which can be used as constituents of such liquid crystal phases can be characterized by the formula II

wherein L and E are each a carbocyclic or heterocyclic ring system from the group comprising 1,4-disubstituted benzene and cyclohexane rings, 4,4'-disubstituted biphenyl, phenyl cyclohexane and cyclohexyl cyclohexane systems, 2,5-disubstituted pyrimidine and 1,3-dioxane rings 2,6-disubstituted naphthalene, di- and tetrahydronaphthalene, quinazoline and tetrahydroquinazoline, G is

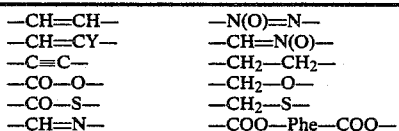

or a C—C single bond, Y is halogen, preferably chlorine, or —CN, and R' and R'' are alkyl, alkoxy, alkanoyloxy or alkoxycarbonyloxy with up to 18, preferably up to 8, carbon atoms, or one of these radicals is also CN, NC, $NO_2$, $CF_3$, F, Cl or Br.

In most of these compounds, R' and R'' are different, one of these radicals usually being an alkyl or alkoxy group. However, other variants of the envisaged substituents are also customary. Many such substances or mixtures thereof are commercially available. All of these substances can be prepared by methods which are known from the literature.

The phases according to the invention contain about 0.1 to 99, preferably 10 to 95%, of one or more compounds of the formula I.

Dielectrics according to the invention containing 0.1 to 40, preferably 0.5 to 30%, of one or more compounds of the formula I are furthermore preferred.

The dielectrics according to the invention are prepared in a manner which is customary per se. As a rule, the components are dissolved in one another, advantageously at elevated temperature.

The liquid crystal dielectrics according to the invention can be modified by suitable additives such that they can be used in all the types of liquid crystal display elements which have hitherto been disclosed.

Such additives are known to the expert and are described in detail in the literature. For example, it is possible to add conductive salts, preferably ethyl-dimethyldodecyl-ammonium 4-hexyloxybenzoate, tetrabutylammonium tetraphenylboranate or complex salts of crown ethers (compare, for example, I. Haller et al., Mol. Cryst. Liq. Cryst. Volume 24, pages 249–258 (1973)) to improve the conductivity, dichroic dyestuffs for the preparation of colored guest/host systems or substances for modifying the dielectric anisotropy, the viscosity and/or the orientation of the nematic phases. Substances of this type are described, for example, in German Offenlegungsschriften 2,209,127, 2,240,864, 2,321,632, 2,338,281, 2,450,088, 2,637,430, 2,853,728 and 2,902,177.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance.

"Customary working up" means: water is added, the mixture is extracted with methylene chloride, the organic phase is separated off, dried and evaporated and the product is purified by crystallization and/or chromatography.

EXAMPLE 1

3.2 g of n-heptylmalondialdehyde tetraethyl acetal, 3.9 g of 4-(trans,trans-4-n-pentylbicyclohexy-4'-yl)benzamidine hydrochloride and 5 ml of dimethyl formamide (DMF) are heated at 150° for 12 hours.

Customary working up gives 4 g of 2-[4-(trans,trans-4-n-pentylbicyclohex-4'-yl)-phenyl]-5-n-heptylpyrimidine.

The following compounds are prepared analogously:

2-[4-(trans,trans-4-Pentylbicyclohex-4'-yl)phenyl]-5-ethylpyrimidine

2-[4-(trans,trans-4-Pentylbicyclohex-4'-yl)phenyl]-5-propylpyrimidine

2-[4-(trans,trans-4-Pentylbicyclohex-4'-yl)phenyl]-5-butylpyrimidine

2-[4-(trans,trans-4-Pentylbicyclohex-4'-yl)phenyl]-5-pentylpyrimidine

2-[4-(trans,trans-4-Pentylbicyclohex-4'-yl)phenyl]-5-octylpyrimidine

2-[4-(trans,trans-4-Pentylbicyclohex-4'-yl)phenyl]-5-decylpyrimidine

2-[4-(trans,trans-4-Pentylbicyclohex-4'-yl)phenyl]-5-dodecylpyrimidine

2-[4-(trans,trans-4-Pentylbicyclohex-4'-yl)phenyl]-5-ethoxypyrimidine

2-[4-(trans,trans-4-Pentylbicyclohex-4'-yl)phenyl]-5-propoxypyrimidine

2-[4-(trans,trans-4-Pentylbicyclohex-4'-yl)phenyl]-5-butoxypyrimidine

2-[4-(trans,trans-4-Pentylbicyclohex-4'-yl)phenyl]-5-pentoxypyrimidine

2-[4-(trans,trans-4-Pentylbicyclohex-4'-yl)phenyl]-5-hexoxypyrimidine

2-[4-(trans,trans-4-Pentylbicyclohex-4'-yl)phenyl]-5-heptoxypyrimidine

2-[4-(trans,trans-4-Pentylbicyclohex-4'-yl)phenyl]-5-octoxypyrimidine
2-[4-(trans,trans-4-Pentylbicyclohex-4'-yl)phenyl]-5-decoxypyrimidine
2-[4-(trans,trans-4-Pentylbicyclohex-4'-yl)phenyl]-5-dodecoxypyrimidine

EXAMPLE 2

2.9 g of n-propylmalondialdehyde tetraethyl acetal, 4.0 g of 4-n-pentyl-trans,trans,trans-p-tercyclohexyl-4'''-carbamidin hydrochloride and 5 ml of DMF are heated at 150° 15 hours. After customary working up, 2-(4-n-Pentyl-trans,trans,trans-p-tercyclohex-4''-yl)-5-n-propylpyrimidine is obtained.

The following compounds are prepared analogously:
2-(4-n-Pentyl-trans,trans,trans-p-tercyclohex-4''-yl)-5-ethylpyrimidine
2-(4-n-Pentyl-trans,trans,trans-p-tercyclohex-4''-yl)-5-butylpyrimidine
2-(4-n-Pentyl-trans,trans,trans-p-tercyclohex-4''-yl)-5-pentylpyrimidine
2-(4-n-Pentyl-trans,trans,trans-p-tercyclohex-4''-yl)-5-octylpyrimidine
2-(4-n-Pentyl-trans,trans,trans-p-tercyclohex-4''-yl)-5-decylpyrimidine
2-(4-n-Pentyl-trans,trans,trans-p-tercyclohex-4''-yl)-5-dodecylpyrimidine
2-(4-n-Pentyl-trans,trans,trans-p-tercyclohex-4''-yl)-5-ethoxypyrimidine
2-(4-n-Pentyl-trans,trans,trans-p-tercyclohex-4''-yl)-5-propoxypyrimidine
2-(4-n-Pentyl-trans,trans,trans-p-tercyclohex-4''-yl)-5-butoxypyrimidine
2-(4-n-Pentyl-trans,trans,trans-p-tercyclohex-4''-yl)-5-pentoxypyrimidine
2-(4-n-Pentyl-trans,trans,trans-p-tercyclohex-4''-yl)-5-hexoxypyrimidine
2-(4-n-Pentyl-trans,trans,trans-p-tercyclohex-4''-yl)-5-heptoxypyrimidine
2-(4-n-Pentyl-trans,trans,trans-p-tercyclohex-4''-yl)-5-octoxypyrimidine
2-(4-n-Pentyl-trans,trans,trans-p-tercyclohex-4''-yl)-5-decoxypyrimidine
2-(4-n-Pentyl-trans,trans,trans-p-tercyclohex-4''-yl)-5-dodecoxypyrimidine

EXAMPLE 3

2-[4-trans-4-n-Hexylcyclohexyl)-phenyl]-5-(trans-4-n-propylcyclohexyl)-pyrimidine is obtained analogously to examples 1 and 2 from 4-(trans-4-n-hexylcyclohexyl)benzamidin hydrochloride and trans-4-n-propylcyclohexylmalondialdehyde tetramethyl acetal (obtainable from trans-4-n-propylcyclohexanecarbaldehyde by a Wittig reaction with methoxymethyltriphenylphosphonium chloride/potassium tertiary butylate and reaction of the resulting enol ether with methyl orthoformate boron trifluoride-etherate).

The following compounds are prepared analogously:
2-[4-(trans-4-Hexylcyclohexyl)-phenyl]-5-(trans-4-ethylcyclohexyl)-pyrimidine
2-[4-(trans-4-Hexylcyclohexyl)-phenyl]-5-(trans-4-butylcyclohexyl)-pyrimidine
2-[4-(trans-4-Hexylcyclohexyl)-phenyl]-5-(trans-4-pentylcyclohexyl)-pyrimidine
2-[4-(trans-4-Hexylcyclohexyl)-phenyl]-5-(trans-4-heptylcyclohexyl)-pyrimidine
2-[4-(trans-4-Hexylcyclohexyl)-phenyl]-5-(trans-4-octylcyclohexyl)-pyrimidine
2-[4-(trans-4-Hexylcyclohexyl)-phenyl]-5-(trans-4-nonylcyclohexyl)-pyrimidine
2-[4-(trans-4-Hexylcyclohexyl)-phenyl]-5-(trans-4-decylcyclohexyl)-pyrimidine
2-[4-(trans-4-Ethylcyclohexyl)-phenyl]-5-(trans-4-ethylcyclohexyl)-pyrimidine
2-[4-(trans-4-Ethylcyclohexyl)-phenyl]-5-(trans-4-propylcyclohexyl)-pyrimidine
2-[4-(trans-4-Ethylcyclohexyl)-phenyl]-5-(trans-4-butylcyclohexyl)-pyrimidine
2-[4-(trans-4-Ethylcyclohexyl)-phenyl]-5-(trans-4-pentylcyclohexyl)-pyrimidine
2-[4-(trans-4-Ethylcyclohexyl)-phenyl]-5-(trans-4-heptylcyclohexyl)-pyrimidine
2-[4-(trans-4-Ethylcyclohexyl)-phenyl]-5-(trans-4-octylcyclohexyl)-pyrimidine
2-[4-(trans-4-Ethylcyclohexyl)-phenyl]-5-(trans-4-nonylcyclohexyl)-pyrimidine
2-[4-(trans-4-Ethylcyclohexyl)-phenyl]-5-(trans-4-decylcyclohexyl)-pyrimidine
2-[4-(trans-4-Propylcyclohexyl)-phenyl]-5-(trans-4-ethylcyclohexyl)-pyrimidine
2-[4-(trans-4-Propylcyclohexyl)-phenyl]-5-(trans-4-propylcyclohexyl)-pyrimidine
2-[4-(trans-4-Propylcyclohexyl)-phenyl]-5-(trans-4-butylcyclohexyl)-pyrimidine
2-[4-(trans-4-Propylcyclohexyl)-phenyl]-5-(trans-4-pentylcyclohexyl)-pyrimidine
2-[4-(trans-4-Propylcyclohexyl)-phenyl]-5-(trans-4-heptylcyclohexyl)-pyrimidine
2-[4-(trans-4-Propylcyclohexyl)-phenyl]-5-(trans-4-octylcyclohexyl)-pyrimidine
2-[4-(trans-4-Propylcyclohexyl)-phenyl]-5-(trans-4-nonylcyclohexyl)-pyrimidine
2-[4-(trans-4-Propylcyclohexyl)-phenyl]-5-(trans-4-decylcyclohexyl)-pyrimidine
2-[4-(trans-4-Pentylcyclohexyl)-phenyl]-5-(trans-4-ethylcyclohexyl)-pyrimidine
2-[4-(trans-4-Pentylcyclohexyl)-phenyl]-5-(trans-4-propylcyclohexyl)-pyrimidine
2-[4-(trans-4-Pentylcyclohexyl)-phenyl]-5-(trans-4-butylcyclohexyl)-pyrimidine
2-[4-(trans-4-Pentylcyclohexyl)-phenyl]-5-(trans-4-pentylcyclohexyl)-pyrimidine
2-[4-(trans-4-Pentylcyclohexyl)-phenyl]-5-(trans-4-heptylcyclohexyl)-pyrimidine
2-[4-(trans-4-Pentylcyclohexyl)-phenyl]-5-(trans-4-octylcyclohexyl)-pyrimidine
2-[4-(trans-4-Pentylcyclohexyl)-phenyl]-5-(trans-4-nonylcyclohexyl)-pyrimidine
2-[4-(trans-4-Pentylcyclohexyl)-phenyl]-5-(trans-4-decylcyclohexyl)-pyrimidine
2-[4-(trans-4-Heptylcyclohexyl)-phenyl]-5-(trans-4-ethylcyclohexyl)-pyrimidine
2-[4-(trans-4-Heptylcyclohexyl)-phenyl]-5-(trans-4-propylcyclohexyl)-pyrimidine
2-[4-(trans-4-Heptylcyclohexyl)-phenyl]-5-(trans-4-butylcyclohexyl)-pyrimidine
2-[4-(trans-4-Heptylcyclohexyl)-phenyl]-5-(trans-4-pentylcyclohexyl)-pyrimidine
2-[4-(trans-4-Heptylcyclohexyl)-phenyl]-5-(trans-4-heptylcyclohexyl)-pyrimidine
2-[4-(trans-4-Heptylcyclohexyl)-phenyl]-5-(trans-4-octylcyclohexyl)-pyrimidine
2-[4-(trans-4-Heptylcyclohexyl)-phenyl]-5-(trans-4-nonylcyclohexyl)-pyrimidine
2-[4-(trans-4-Heptylcyclohexyl)-phenyl]-5-(trans-4-decylcyclohexyl)-pyrimidine

EXAMPLE 4

Trans,trans-4-n-heptylbicyclohex-4'-yl-malondialdeyde tetramethyl acetal can be obtained analogously to Example 3 from trans,trans-4-n-heptylbicyclohexyl-4'-carbaldehyde (from the corresponding acid chloride by Rosenmund reduction), and 2-(trans-4-n-pentylcyclohexyl)-5-(trans,trans-4-n-heptylbicyclohex-4'-yl)-pyrimidine is obtained therefrom by reaction with trans-4-n-pentylcyclohexane carbamidine hydrochloride analogously to Examples 1 and 2.

The following compounds are prepared analogously:
2-(trans-4-Pentylcyclohexyl)-5-(trans,trans-4-ethylbicyclohex-4'-yl)-pyrimidine
2-(trans-4-Pentylcyclohexyl)-5-(trans,trans-4-propylbicyclohex-4'-yl)-pyrimidine
2-(trans-4-Pentylcyclohexyl)-5-(trans,trans-4-butylbicyclohex-4'-yl)-pyrimidine
2-(trans-4-Pentylcyclohexyl)-5-(trans,trans-4-pentylbicyclohex-4'-yl)-pyrimidine
2-(trans-4-Pentylcyclohexyl)-5-(trans,trans-4-heptylbicyclohex-4'-yl)-pyrimidine
2-(trans-4-Pentylcyclohexyl)-5-(trans,trans-4-octylbicyclohex-4'-yl)-pyrimidine
2-(trans-4-Pentylcyclohexyl)-5-(trans,trans-4-nonylbicyclohex-4'-yl)-pyrimidine
2-(trans-4-Pentylcyclohexyl)-5-(trans,trans-4-decylbicyclohex-4'-yl)-pyrimidine
2-(trans-4-Propylcyclohexyl)-5-(trans,trans-4-ethylbicyclohex-4'-yl)-pyrimidine
2-trans-4-Propylcyclohexyl)-5-(trans,trans-4-propylbicyclohex-4'-yl)-pyrimidine
2-(trans-4-Propylcyclohexyl)-5-(trans,trans-4-butylbicyclohex-4'-yl)-pyrimidine
2-(trans-4-Propylcyclohexyl)-5-(trans,trans-4-pentylbicyclohex-4'-yl)-pyrimidine
2-(trans-4-Propylcyclohexyl)-5-(trans,trans-4-heptylbicyclohex-4'-yl)-pyrimidine
2-(trans-4-Propylcyclohexyl)-5-(trans,trans-4-octylbicyclohex-4'-yl)-pyrimidine
2-(trans-4-Propylcyclohexyl)-5-(trans,trans-4-nonylbicyclohex-4'-yl)-pyrimidine
2-(trans-4-Propylcyclohexyl)-5-(trans,trans-4-decylbicyclohex-4'-yl)-pyrimidine
2-(trans-4-Butylcyclohexyl)-5-(trans,trans-4-ethylbicyclohex-4'-yl)-pyrimidine
2-(trans-4-Butylcyclohexyl)-5-(trans,trans-4-propylbicyclohex-4'-yl)-pyrimidine
2-(trans-4-Butylcyclohexyl)-5-(trans,trans-4-butylbicyclohex-4'-yl)-pyrimidine
2-(trans-4-Butylcyclohexyl)-5-(trans,trans-4-pentylbicyclohex-4'-yl)-pyrimidine
2-(trans-4-Butylcyclohexyl)-5-(trans,trans-4-heptylbicyclohex-4'-yl)-pyrimidine
2-(trans-4-Butylcyclohexyl)-5-(trans,trans-4-octylbicyclohex-4'-yl)-pyrimidine
2-(trans-4-Butylcyclohexyl)-5-(trans,trans-4-nonylbicyclohex-4'-yl)-pyrimidine
2-(trans-4-Butylcyclohexyl)-5-(trans,trans-4-decylbicyclohex-4'-yl)-pyrimidine
2-(trans-4-Heptylcyclohexyl)-5-(trans,trans-4-ethylbicyclohex-4'-yl)-pyrimidine
2-(trans-4-Heptylcyclohexyl)-5-(trans,trans-4-propylbicyclohex-4'-yl)-pyrimidine
2-(trans-4-Heptylcyclohexyl)-5-(trans,trans-4-butylbicyclohex-4'-yl)-pyrimidine
2-(trans-4-Heptylcyclohexyl)-5-(trans,trans-4-pentylbicyclohex-4'-yl)-pyrimidine
2-(trans-4-Heptylcyclohexyl)-5-(trans,trans-4-heptylbicyclohex-4'-yl)-pyrimidine
2-(trans-4-Heptylcyclohexyl)-5-(trans,trans-4-octylbicyclohex-4'-yl)-pyrimidine
2-(trans-4-Heptylcyclohexyl)-5-(trans,trans-4-nonylbicyclohex-4'-yl)-pyrimidine
2-(trans-4-Heptylcyclohexyl)-5-(trans,trans-4-decylbicyclohex-4'-yl)-pyrimidine

EXAMPLE 5

2.8 g of trans,trans-4-n-butylbicyclohexyl-4'-carbonyl chloride, 2.3 g of 2-(4-hydroxyphenyl)-5-n-butylpyrimidine and 0.8 g of pyridine are heated at 100° in 20 ml of toluene for 3 hours. After cooling, the pyridine hydrochloride is filtered off with suction. Customary working up gives 3.2 g of 2-[4-(4-trans,trans-n-butylbicyclohex-4'-yl-carbonyloxy)-phenyl]-5-n-butylpyrimidine.

The following compounds are prepared analogously
2-[4-(4-trans,trans-Ethylbicyclohex-4'-ylcarbonyloxy)-phenyl]-5-butylpyrimidine
2-[4-(4-trans,trans-Propylbicyclohex-4'-ylcarbonyloxy)-phenyl]-5-butylpyrimidine
2-[4-(4-trans,trans-Pentylbicyclohex-4'-ylcarbonyloxy)-phenyl]-5-butylpyrimidine
2-[4-(4-trans,trans-Heptylbicyclohex-4'-ylcarbonyloxy)-phenyl]-5-butylpyrimidine
2-[4-(4-trans,trans-Octylbicyclohex-4'-ylcarbonyloxy)-phenyl]-5-butylpyrimidine
2-[4-(4-trans,trans-Nonylbicyclohex-4'-ylcarbonyloxy)-phenyl]-5-butylpyrimidine
2-[4-(4-trans,trans-Decylbicyclohex-4'-ylcarbonyloxy)-phenyl]-5-butylpyrimidine
2-[4-(4-trans,trans-Cyanbicyclohex-4'-ylcarbonyloxy)-phenyl]-5-butylpyrimidine
2-[4-(4-trans,trans-Ethylbicyclohex-4'-ylcarbonyloxy)-phenyl]-5-propylpyrimidine
2-[4-(4-trans,trans-Propylbicyclohex-4'-ylcarbonyloxy)-phenyl]-5-propylpyrimidine
2-[4-(4-trans,trans-Butylbicyclohex-4'-ylcarbonyloxy)-phenyl]-5-propylpyrimidine
2-[4-(4-trans,trans-Pentylbicyclohex-4'-ylcarbonyloxy9-phenyl]-5-propylpyrimidine]
2-[4-(4-trans,trans-Heptylbicyclohex-4'-ylcarbonyloxy)-phenyl]-5-propylpyrimidine
2-[4-(4-trans,trans-Octylbicyclohex-4'-ylcarbonyloxy)-phenyl]-5-propylpyrimidine
2-[4-(4-trans,trans-Nonylbicyclohex-4'-ylcarbonyloxy)-phenyl]-5-propylpyrimidine
2-[4-(4-trans,trans-Decylbicyclohex-4'-ylcarbonyloxy)-phenyl]-5-propylpyrimidine
2-[4-(4-trans,trans-Ethylbicyclohex-4'-ylcarbonyloxy)-phenyl]-5-pentylpyrimidine
2-[4-(4-trans,trans-Propylbicyclohex-4'-ylcarbonyloxy)-phenyl]-5-pentylpyrimidine
2-[4-(4-trans,trans-Butylbicyclohex-4'-ylcarbonyloxy)-phenyl]-5-pentylpyrimidine
2-[4-(4-trans,trans-Pentylbicyclohex-4'-ylcarbonyloxy)-phenyl]-5-pentylpyrimidine
2-[4-(4-trans,trans-Heptylbicyclohex-4'-ylcarbonyloxy)-phenyl]-5-pentylpyrimidine
2-[4-(4-trans,trans-Octylbicyclohex-4'-ylcarbonyloxy)-phenyl]-5-pentylpyrimidine
2-[4-(4-trans,trans-Nonylbicyclohex-4'-ylcarbonyloxy)-phenyl]-5-pentylpyrimidine
2-[4-(4-trans,trans-Decylbicyclohex-4'-ylcarbonyloxy)-phenyl]-5-pentylpyrimidine 2-[4-(4-trans,trans-Ethylbicyclohex-4'-ylcarbonyloxy)-phenyl]-5-heptylpyrimidine
2-[4-(4-trans,trans-Propylbicyclohex-4'-ylcarbonyloxy)-phenyl]-5-heptylpyrimidine
2-[4-(4-trans,trans-Butylbicyclohex-4'-ylcarbonyloxy)-phenyl]-5-heptylpyrimidine
2-[4-(4-trans,trans-Pentylbicyclohex-4'-ylcarbonyloxy)-phenyl]-5-heptylpyrimidine
2-[4-(4-trans,trans-Heptylbicyclohex-4'-ylcarbonyloxy)-phenyl]-5-heptylpyrimidine
2-[4-(4-trans,trans-Octylbicyclohex-4'-ylcarbonyloxy)-phenyl]-5-heptylpyrimidine
2-[4-(4-trans,trans-Nonylbicyclohex-4'-ylcarbonyloxy)-phenyl]-5-heptylpyrimidine
2-[4-(4-trans,trans-Decylbicyclohex-4'-ylcarbonyloxy)-phenyl]-5-heptylpyrimidine
2-[4-(4-trans,trans-Ethylbicyclohex-4'-ylcarbonyloxy)-phenyl]-5-nonylpyrimidine
2-[4-(4-trans,trans-Propylbicyclohex-4'-ylcarbonyloxy)-phenyl]-5-nonylpyrimidine
2-[4-(4-trans,trans-Butylbicyclohex-4'-ylcarbonyloxy)-phenyl]-5-nonylpyrimidine
2-[4-(4-trans,trans-Pentylbicyclohex-4'-ylcarbonyloxy)-phenyl]-5-nonylpyrimidine
2-[4-(4-trans,trans-Heptylbicyclohex-4'-ylcarbonyloxy)-phenyl]-5-nonylpyrimidine
2-[4-(4-trans,trans-Octylbicyclohex-4'-ylcarbonyloxy)-phenyl]-5-nonylpyrimidine
2-[4-(4-trans,trans-Nonylbicyclohex-4'-ylcarbonyloxy)-phenyl]-5-nonylpyrimidine
2-[4-(4-trans,trans-Decylbicyclohex-4'-ylcarbonyloxy)-phenyl]-5-nonylpyrimidine
2-[4-(4-trans,trans-Ethylbicyclohex-4'-ylcarbonyloxy)-phenyl]-5-dodecylpyrimidine
2-[4-(4-trans,trans-Propylbicyclohex-4'-ylcarbonyloxy)-phenyl]-5-dodecylpyrimidine
2-[4-(4-trans,trans-Butylbicyclohex-4'-ylcarbonyloxy)-phenyl]-5-dodecylpyrimidine
2-[4-(4-trans,trans-Pentylbicyclohex-4'-ylcarbonyloxy)-phenyl]-5-dodecylpyrimidine
2-[4-(4-trans,trans-Heptylbicyclohex-4'-ylcarbonyloxy)-phenyl]-5-dodecylpyrimidine
2-[4-(4-trans,trans-Octylbicyclohex-4'-ylcarbonyloxy)-phenyl]-5-dodecylpyrimidine
2-[4-(4-trans,trans-Nonylbicyclohex-4'-ylcarbonyloxy)-phenyl]-5-dodecylpyrimidine
2-[4-(4-trans,trans-Decylbicyclohex-4'-ylcarbonyloxy)-phenyl]-5-dodecylpyrimidine
2-[4-(4-trans,trans-Ethylbicyclohex-4'-ylcarbonyloxy)-phenyl]-5-heptoxypyrimidine
2-[4-(4-trans,trans-Propylbicyclohex-4'-ylcarbonyloxy)-phenyl]-5-heptoxypyrimidine
2-[4-(4-trans,trans-Butylbicyclohex-4'-ylcarbonyloxy)-phenyl]-5-heptoxypyrimidine
2-[4-(4-trans,trans-Pentylbicyclohex-4'-ylcarbonyloxy)-phenyl]-5-heptoxypyrimidine
2-[4-(4-trans,trans-Heptylbicyclohex-4'-ylcarbonyloxy)-phenyl]-5-heptoxypyrimidine
2-[4-(4-trans,trans-Octylbicyclohex-4'-ylcarbonyloxy)-phenyl]-5-heptoxypyrimidine
2-[4-(4-trans,trans-Nonylbicyclohex-4'-carbonyloxy)-phenyl]-5-heptoxypyrimidine
2-[4-(4-trans,trans-Decylbicyclohex-4'-ylcarbonyloxy)-phenyl]-5-heptoxypyrimidine
2-[4-(4-trans,trans-Ethylbicyclohex-4'-ylcarbonyloxy)-phenyl]-5-cyanpyrimidine
2-[4-(4-trans,trans-Propylbicyclohex-4'-ylcarbonyloxy)-phenyl]-5-cyanpyrimidine
2-[4-(4-trans,trans-Butylbicyclohex-4'-ylcarbonyloxy)-phenyl]-5-cyanpyrimidine
2-[4-(4-trans,trans-Pentylbicyclohex-4'-ylcarbonyloxy)-phenyl]-5-cyanpyrimidine
2-[4-(4-trans,trans-Heptylbicyclohex-4'-ylcarbonyloxy)-phenyl]-5-cyanpyrimidine
2-[4-(4-trans,trans-Octylbicyclohex-4'-ylcarbonyloxy)-phenyl]-5-cyanpyrimidine
2-[4-(4-trans,trans-Nonylbicyclohex-4'-ylcarbonyloxy)-phenyl]-5-cyanpyrimidine
2-[4-(4-trans,trans-Decylbicyclohex-4'-ylcarbonyloxy)-phenyl]-5-cyanpyrimidine
2-[4-(4-trans-Ethylcyclohexyl-p-phenylcarbonyloxy)-phenyl]-5-pentylpyrimidine
2-[4-(4-trans-Propylcyclohexyl-p-phenylcarbonyloxy)-phenyl]-5-pentylpyrimidine
2-[4-(4-trans-Butylcyclohexyl-p-phenylcarbonyloxy)-phenyl]-5-pentylpyrimidine
2-[4-(4-trans-Pentylcyclohexyl-p-phenylcarbonyloxy)-phenyl]-5-pentylpyrimidine
2-[4-(4-trans-Heptylcyclohexyl-p-phenylcarbonyloxy)-phenyl]-5-pentylpyrimidine
2-[4-(4-trans-Octylcyclohexyl-p-phenylcarbonyloxy)-phenyl]-5-pentylpyrimidine
2-[4-(4-trans-Nonylcyclohexyl-p-phenylcarbonyloxy)-phenyl]-5-pentylpyrimidine
2-[4-(4-trans-Decylcyclohexyl-p-phenylcarbonyloxy)-phenyl]-5-pentylpyrimidine
2-[4-(4-trans-Ethylcyclohexyl-p-phenylcarbonyloxy)-phenyl]-5-cyanpyrimidine
2-[4-(4-trans-Propylcyclohexyl-p-phenylcarbonyloxy)-phenyl]-5-cyanpyrimidine 2-[4-(4-trans-Butylcyclohexyl-p-phenylcarbonyloxy)-phenyl]-5-cyanpyrimidine
2-[4-(4-trans-Pentylcyclohexyl-p-phenylcarbonyloxy)-phenyl]-5-cyanpyrimidine
2-[4-(4-trans-Heptylcyclohexyl-p-phenylcarbonyloxy)-phenyl]-5-cyanpyrimidine
2-[4-(4-trans-Octylcyclohexyl-p-phenylcarbonyloxy)-phenyl]-5-cyanpyrimidine
2-[4-(4-trans-Nonylcyclohexyl-p-phenylcarbonyloxy)-phenyl]-5-cyanpyrimidine
2-[4-(4-trans-Decylcyclohexyl-p-phenylcarbonyloxy)-phenyl]-5-cyanpyrimidine

EXAMPLE 6

Esterification of 2-(4-hydroxyphenyl)-5-(trans-4-n-heptyl-cyclohexyl)-pyrimidine with trans-4-n-propyl-cyclohexanecarboxylic acid chloride analogously to Example 5 gives 2-[4-(trans-4-n-propylcyclohexylcarbonyloxy)-phenyl]-5-trans-4-n-heptylcyclohexyl)-pyrimidine.

The following compounds are prepared analogously:
2-[4-(trans-4-Propylcyclohexylcarbonyloxy)-phenyl]-5-(trans-4-ethylcyclohexyl)-pyrimidine
2-[4-(trans-4-Propylcyclohexylcarbonyloxy)-phenyl]-5-(trans-4-propylcyclohexyl)-pyrimidine
2-[4-(trans-4-Propylcyclohexylcarbonyloxy)-phenyl]-5-(trans-4-butylcyclohexyl)-pyrimidine
2-[4-(trans-4-Propylcyclohexylcarbonyloxy)-phenyl]-5-(trans-4-pentylcyclohexyl)-pyrimidine
2-[4-(trans-4-Propylcyclohexylcarbonyloxy)-phenyl]-5-(trans-4-octylcyclohexyl)-pyrimidine
2-[4-(trans-4-Propylcyclohexylcarbonyloxy)-phenyl]-5-(trans-4-nonylcyclohexyl)-pyrimidine
2-[4-(trans-4-Propylcyclohexylcarbonyloxy)-phenyl]-5-(trans-4-decylcyclohexyl)-pyrimidine 2-[4-(trans-4-Butylcyclohexylcarbonyloxy)-phenyl]-5-(trans-4-ethylcyclohexyl)-pyrimidine
2-[4-(trans-4-Butylcyclohexylcarbonyloxy)-phenyl]-5-(trans-4-propylcyclohexyl)-pyrimidine
2-[4-(trans-4-Butylcyclohexylcarbonyloxy)-phenyl]-5-(trans-4-butylcyclohexyl)-pyrimidine
2-[4-(trans-4-Butylcyclohexylcarbonyloxy)-phenyl]-5-(trans-4-pentylcyclohexyl)-pyrimidine
2-[4(trans-4-Butylcyclohexylcarbonyloxy)-phenyl]-5-(trans-4-heptylcyclohexyl)-pyrimidine
2-[4-(trans-4-Butylcyclohexylcarbonyloxy)-phenyl]-5-(trans-4-octylcyclohexyl)-pyrimidine
2-[4-(trans-4-Butylcyclohexylcarbonyloxy)-phenyl]-5-(trans-4-nonylcyclohexyl)-pyrimidine
2-[4-(trans-4-Butylcyclohexylcarbonyloxy)-phenyl]-5-(trans-4-decylcyclohexyl)-pyrimidine
2-[4-(trans-4-Pentylcyclohexylcarbonyloxy)-phenyl]-5-(trans-4-ethylcyclohexyl)-pyrimidine
2-[4-(trans-4-Pentylcyclohexylcarbonyloxy)-phenyl]-5-(trans-4-propylcyclohexyl)-pyrimidine
2-[4-(trans-4-Pentylcyclohexylcarbonyloxy)-phenyl]-5-(trans-4-butylcyclohexyl)-pyrimidine
2-[4-(trans-4-Pentylcyclohexylcarbonyloxy)-phenyl]-5-(trans-4-pentylcyclohexyl)-pyrimidine
2-[4-(trans-4-Pentylcyclohexylcarbonyloxy)-phenyl]-5-(trans-4-heptylcyclohexyl)-pyrimidine
2-[4-(trans-4-Pentylcyclohexylcarbonyloxy)-phenyl]-5-(trans-4-octylcyclohexyl)-pyrimidine
2-[4-(trans-4-Pentylcyclohexylcarbonyloxy)-phenyl]-5-(trans-4-nonylcyclohexyl)-pyrimidine
2-[4-(trans-4-Pentylcyclohexylcarbonyloxy)-phenyl]-5-(trans-4-decylcyclohexyl)-pyrimidine
2-[4-(trans-4-Heptylcyclohexylcarbonyloxy)-phenyl]-5-(trans-4-ethylcyclohexyl)-pyrimidine
2-[4-(trans-4-Heptylcyclohexylcarbonyloxy)-phenyl]-5-(trans-4-propylcyclohexyl)-pyrimidine
2-[4-(trans-4-Heptylcyclohexylcarbonyloxy)-phenyl]-5-(trans-4-butylcyclohexyl)-pyrimidine
2-[4-(trans-4-Heptylcyclohexylcarbonyloxy)-phenyl]-5-(trans-4-pentylcyclohexyl)-pyrimidine
2-[4-(trans-4-Heptylcyclohexylcarbonyloxy)-phenyl]-5-(trans-4-heptylcyclohexyl)-pyrimidine
2-[4-(trans-4-Heptylcyclohexylcarbonyloxy)-phenyl]-5-(trans-4-octylcyclohexyl)-pyrimidine
2-[4-(trans-4-Heptylcyclohexylcarbonyloxy)-phenyl]-5-(trans-4-nonylcyclohexyl)-pyrimidine
2-[4-(trans-4-Heptylcyclohexylcarbonyloxy)-phenyl]-5-(trans-4-decylcyclohexyl)-pyrimidine
2-[4-(4-Cyanphenylcarbonyloxy)-phenyl]-5-(trans-4-ethylcyclohexyl)-pyrimidine
2-[4-(4-Cyanphenylcarbonyloxy)-phenyl]-5-(trans-4-propylcyclohexyl)-pyrimidine
2-[4-(4-Cyanphenylcarbonyloxy)-phenyl]-5-(trans-4-butylcyclohexyl)-pyrimidine
2-[4-(4-Cyanphenylcarbonyloxy)-phenyl]-5-(trans-4-pentylcyclohexyl)-pyrimidine
2-[4-(4-Cyanphenylcarbonyloxy)-phenyl]-5-(trans-4-heptylcyclohexyl)-pyrimidine
2-[4-(4-Cyanphenylcarbonyloxy)-phenyl]-5-(trans-4-octylcyclohexyl)-pyrimidine
2-[4-(4-Cyanphenylcarbonyloxy)-phenyl]-5-(trans-4-nonylcyclohexyl)-pyrimidine
2-[4-(4-Cyanphenylcarbonyloxy)-phenyl]-5-(trans-4-decylcyclohexyl)-pyrimidine
2-[4-(4-Ethoxyphenylcarbonyloxy)-phenyl]-5-(trans-4-ethylcyclohexyl)-pyrimidine
2-[4-(4-Ethoxyphenylcarbonyloxy)-phenyl]-5-(trans-4-propylcyclohexyl)-pyrimidine
2-[4-(4-Ethoxyphenylcarbonyloxy)-phenyl]-5-(trans-4-butylcyclohexyl)-pyrimidine
2-[4-(4-Ethoxyphenylcarbonyloxy)-phenyl]-5-(trans-4-pentylcyclohexyl)-pyrimidine
2-[4-(4-Ethoxyphenylcarbonyloxy)-phenyl]-5-(trans-4-heptylcyclohexyl)-pyrimidine
2-[4-(4-Ethoxyphenylcarbonyloxy)-phenyl]-5-(trans-4-octylcyclohexyl)-pyrimidine
2-[4-(4-Ethoxyphenylcarbonyloxy)-phenyl]-5-(trans-4-nonylcyclohexyl)-pyrimidine
2-[4-(4-Ethoxyphenylcarbonyloxy)-phenyl]-5-(trans-4-decylcyclohexyl)-pyrimidine
2-[4-(trans-2-Pentyl-1,3-dioxan-5-ylcarbonyloxy)-phenyl]-5-(trans-4-ethylcyclohexyl)-pyrimidine
2-[4-(trans-2-Pentyl-1,3-dioxan-5-ylcarbonyloxy)-phenyl]-5-(trans-4-propylcyclohexyl)-pyrimidine
2-[4-(trans-2-Pentyl-1,3-dioxan-5-ylcarbonyloxy)-phenyl]-5-(trans-4-butylcyclohexyl)-pyrimidine
2-[4-(trans-2-Pentyl-1,3-dioxan-5-ylcarbonyloxy)-phenyl]-5-(trans-4-pentylcyclohexyl)-pyrimidine
2-[4-(trans-2-Pentyl-1,3-dioxan-5-ylcarbonyloxy)-phenyl]-5-(trans-4-heptylcyclohexyl)-pyrimidine
2-[4-(trans-2-Pentyl-1,3-dioxan-5-ylcarbonyloxy)-phenyl]-5-(trans-4-octylcyclohexyl)-pyrimidine
2-[4-(trans-2-Pentyl-1,3-dioxan-5-ylcarbonyloxy)-phenyl]-5-(trans-4-nonylcyclohexyl)-pyrimidine
2-[4-(trans-2-Pentyl-1,3-dioxan-5-ylcarbonyloxy)-phenyl]-5-(trans-4-decylcyclohexyl)-pyrimidine
2-[4-(trans-2-Pentyl-1,3-dithian-5-ylcarbonyloxy)-phenyl]-5-(trans-4-ethylcyclohexyl)-pyrimidine
2-[4-(trans-2-Pentyl-1,3-dithian-5-ylcarbonyloxy)-phenyl]-5-(trans-4-propylcyclohexyl)-pyrimidine
2-[4-(trans-2-Pentyl-1,3-dithian-5-ylcarbonyloxy)-phenyl]-5-(trans-4-butylcyclohexyl)-pyrimidine
2-[4-(trans-2-Pentyl-1,3-dithian-5-ylcarbonyloxy)-phenyl]-5-(trans-4-pentylcyclohexyl)-pyrimidine
2-[4-(trans-2-Pentyl-1,3-dithian-5-ylcarbonyloxy)-phenyl]-5-(trans-4-heptylcyclohexyl)-pyrimidine
2-[4-(trans-2-Pentyl-1,3-dithian-5-ylcarbonyloxy)-phenyl]-5-(trans-4-octylcyclohexyl)-pyrimidine
2-[4-(trans-2-Pentyl-1,3-dithian-5-ylcarbonyloxy)-phenyl]-5-(trans-4-nonylcyclohexyl)-pyrimidine
2-[4-(trans-2-Pentyl-1,3-dithian-5-ylcarbonyloxy)-phenyl]-5-(trans-4-decylcyclohexyl)-pyrimidine

EXAMPLE 7

Esterification of 2-(4-hydroxyphenyl)-5-[2-(trans-4-n-pentylcyclohexyl)-ethyl]-pyrimidine [obtainable by condensation of 4-hydroxybenzamidine hydrochloride with 2-(trans-4-n-pentylcyclohexyl)-ethylmalondialdehydetetramethyl acetal [obtainable from trans-4-n-pentylcyclohexylpropionaldehyde]] with trans-4-n-pentylcyclohexanecarboxylic acid chloride analogously to Example 5 gives 2-[4-(trans-4-n-pentylcyclohexylcarbonyloxy)-phenyl]-5-[2-(trans-4-n-pentylcyclohexyl)-ethyl]-pyrimidine.

The following compounds are prepared analogously:
2-(4-(trans-4-Pentylcyclohexylcarbonyloxy)-phenyl]-5-[2-(trans-4-ethylcyclohexyl)-ethyl]-pyrimidine
2-[4-(trans-4-Pentylcyclohexylcarbonyloxy)-phenyl]-5-[2-(trans-4-propylcyclohexyl)-ethyl]-pyrimidine
2-[4-(trans-4-Pentylcyclohexylcarbonyloxy)-phenyl]-5-[2-(trans-4-butylcyclohexyl)-ethyl]-pyrimidine
2-[4-(trans-4-Pentylcyclohexylcarbonyloxy)-phenyl]-5-[2-(trans-4-heptylcyclohexyl)-ethyl]-pyrimidine
2-[4-(trans-4-Pentylcyclohexylcarbonyloxy)-phenyl]-5-[2-(trans-4-octylcyclohexyl)-ethyl]-pyrimidine 2-[4-(trans-4-Pentylcyclohexylcarbonyloxy)-phenyl]-5-[2-(trans-4-nonylcyclohexyl)-ethyl]-pyrimidine
2-[4-(trans-4-Pentylcyclohexylcarbonyloxy)-phenyl]-5-[2-(trans-4-decylcyclohexyl)-ethyl]-pyrimidine

EXAMPLE 8

Etherification of 2-(4-hydroxyphenyl)-5-[2-(trans-4-n-pentylcyclohexyl)-ethyl]-pyrimidine (compare Example 7) with trans-4-n-pentylcyclohexylmethyl bromide in dimethylformamide in the presence of potassium carbonate gives 2-[4-(trans-4-n-pentylcyclohexylmethoxy)-phenyl]-5-[2-(trans-4-n-pentylcyclohexyl)-ethyl]-pyrimidine.

The following compounds are prepared analogously:
2-[4-(trans-4-Pentylcyclohexylmethoxy)-phenyl]-5-[2-(trans-4-ethylcyclohexyl)-ethyl]-pyrimidine
2-[4-(trans-4-Pentylcyclohexylmethoxy)-phenyl]-5-[2-(trans-4-propylcyclohexyl)-ethyl]-pyrimidine
2-[4-(trans-4-Pentylcyclohexylmethoxy)-phenyl]-5-[2-(trans-4-butycyclohexyl)-ethyl]-pyrimidine
2-[4-(trans-4-Pentylcyclohexylmethoxy)-phenyl]-5-[2-(trans-4-heptylcyclohexyl)-ethyl]-pyrimidine
2-[4-(trans-4-Pentylcyclohexylmethoxy)-phenyl]-5-[2-(trans-4-octylcyclohexyl)-ethyl]-pyrimidine
2-[4-(trans-4-Pentylcyclohexylmethoxy)-phenyl]-5-[2-(trans-4-nonylcyclohexyl)-ethyl]-pyrimidine
2-[4-(trans-4-Pentylcyclohexylmethoxy)-phenyl]-5-[2-(trans-4-decylcyclohexyl)-ethyl]-pyrimidine

EXAMPLE 9

Heating 4-(trans-4-n-hexylcyclohexyl)-benzamidine hydrochloride with 2-(trans-4-n-propyl-cyclohexyl)-ethylmalondialdehydetetramethyl acetal (obtainable analogously to the pentyl compound in Example 7) and subsequent customary working up gives 2-[4-(trans-n-hexylcyclohexyl)-phenyl]-5-[2-(trans-4-n-propylcyclohexyl)-ethyl]-pyrimidine.

The following compounds are prepared analogously:
2-[4-(trans-4-Hexylcyclohexyl)-phenyl]-5-[2-(trans-4-ethylcyclohexyl)-ethyl]-pyrimidine
2-[4-(trans-4-Hexylcyclohexyl)-phenyl]-5-[2-(trans-4-butylcyclohexyl)-ethyl]-pyrimidine
2-[4-(trans-4-Hexylcyclohexyl)-phenyl]-5-[2-(trans-4-pentylcyclohexyl)-ethyl]-pyrimidine
2-[4-(trans-4-Hexylcyclohexyl)-phenyl]-5-[2-(trans-4-heptylcyclohexyl)-ethyl]-pyrimidine
2-[4-(trans-4-Hexylcyclohexyl)-phenyl]-5-[2-(trans-4-octylcyclohexyl)-ethyl]-pyrimidine
2-[4-(trans-4-Propylcyclohexyl)-phenyl]-5-[2-(trans-4-ethylcyclohexyl)-ethyl]-pyrimidine
2-[4-(trans-4-Propylcyclohexyl)-phenyl]-5-[2-(trans-4-propylcyclohexyl)-ethyl]-pyrimidine
2-[4-(trans-4-Propylcyclohexyl)-phenyl]-5-[2-(trans-4-butylcyclohexyl)-ethyl]-pyrimidine
2-[4-(trans-4-Propylcyclohexyl)-phenyl]-5-[2-(trans-4-pentylcyclohexyl)-ethyl]-pyrimidine
2-[4-(trans-4-Propylcyclohexyl)-phenyl]-5-[2-(trans-4-heptylcyclohexyl)-ethyl]-pyrimidine
2-[4-(trans-4-Propylcyclohexyl)-phenyl]-5-[2-(trans-4-octylcyclohexyl)-ethyl]-pyrimidine

EXAMPLE 10

8.8 g of 1-(trans-4-propylcyclohexyl)-4-[4-(trans-4-n-pentylcyclohexyl)-phenyl]-butane-1,4-dione (prepared by addition, catalysed by thiazolium salts, of trans-4-n-propylcyclohexanecarbaldehyde on to the Mannich base obtained from 4-(trans-4-n-pentylcyclohexyl)-acetophenone, formaldehyde and dimethylamine) and 1.28 ml of 80% strength hydrazine hydrate are heated at 75° in 70 ml of glacial acetic acid for 8 hours, while simultaneously passing air through. The product precipitated after cooling is recrystallised from ethyl acetate. 3.9 g of 3-(trans-4-n-propylcyclohexyl)-6-[4-(trans-4-n-pentylcyclohexyl)-phenyl]-pyridazine are obtained.

The following compounds are prepared analogously:
3-(trans-4-Propylcyclohexyl)-6-[4-(trans-4-ethylcyclohexyl)-phenyl]-pyridazine
3-(trans-4-Propylcyclohexyl)-6-[4-(trans-4-propylcyclohexyl)-phenyl]-pyridazine
3-(trans-4-Propylcyclohexyl)-6-[4-(trans-4-butylcyclohexyl)-phenyl]-pyridazine
3-(trans-4-Propylcyclohexyl)-6-[4-(trans-4-heptylcyclohexyl)-phenyl]-pyridazine
3-(trans-4-Propylcyclohexyl)-6-[4-(trans-4-octylcyclohexyl)-phenyl]-pyridazine
3-(trans-4-Ethylcyclohexyl)-6-[4-(trans-4-ethylcyclohexyl)-phenyl]-pyridazine
3-(trans-4-Ethylcyclohexyl)-6-[4-(trans-4-propylcyclohexyl)-phenyl]-pyridazine
3-(trans-4-Ethylcyclohexyl)-6-[4-(trans-4-butylcyclohexyl)-phenyl]-pyridazine
3-(trans-4-Ethylcyclohexyl)-6-[4-(trans-4-pentylcyclohexyl)-phenyl]-pyridazine
3-(trans-4-Ethylcyclohexyl)-6-[4-(trans-4-heptylcyclohexyl)-phenyl]-pyridazine
3-(trans-4-Ethylcyclohexyl)-6-[4-(trans-4-octylcyclohexyl)-phenyl]-pyridazine
3-(trans-4-Pentylcyclohexyl)-6-[4-(trans-4-ethylcyclohexyl)-phenyl]-pyridazine
3-(trans-4-Pentylcyclohexyl)-6-[4-(trans-4-propylcyclohexyl)-phenyl]-pyridazine
3-(trans-4-Pentylcyclohexyl)-6-[4-(trans-4-butylcyclohexyl)-phenyl]-pyridazine
3-(trans-4-Pentylcyclohexyl)-6-[4-(trans-4-pentylcyclohexyl)-phenyl]-pyridazine
3-(trans-4-Pentylcyclohexyl)-6-[4-(trans-4-heptylcyclohexyl)-phenyl]-pyridazine
3-(trans-4-Pentylcyclohexyl)-6-[4-(trans-4-octylcyclohexyl)-phenyl]-pyridazine The following examples relate to liquid crystal phases according to the invention:

EXAMPLE A

A liquid crystal phase consisting of
4.4% of 4-ethyl-4'-cyanobiphenyl,
3.8% of 4-propyl-4'-cyanobiphenyl,
4.3% of 4-butyl-4'-cyanobiphenyl
3.5% of 4-cyano-4'-(trans-4-pentylcyclohexyl)-biphenyl
1.0% of 4-ethyl-4'-(trans-4-propylcyclohexyl)-biphenyl,
7.5% of 4-ethyl-2'-fluoro-4'-(trans-4-pentylcyclohexyl)-biphenyl,
4.0% of p-propylphenyl p-trans-4-propylcyclohexylbenzoate
3.0% of p-propylphenyl p-trans-4-pentylcyclohexylbenzoate,
10.6% of p-pentylphenyl trans-4-pentylcyclohexanecarboxylate
6.4% of p-ethoxyphenyl trans-4-propylcyclohexane carboxylate
2.5% of 4,4'-bis-(trans-4-propylcyclohexyl)-biphenyl
2.0% of 4-(trans-4-pentylcyclohexyl)-4'-(trans-4-propylcyclohexyl)-biphenyl,
0.5% of 2-[4-(trans,trans-4-pentylbicyclohex-4"-yl)-phenyl]-5-n-heptylpyrimidine, 8.5% of trans-1-p-ethylphenyl-4-propylcyclohexane,
5.0% of trans-1-p-ethoxyphenyl-4-propylcyclohexane,
5.5% of 2-p-hexyloxyphenyl-5-hexylpyrimidine,
5.5% of 2-p-heptyloxyphenyl-5-hexylpyrimidine,
5.5% of 2-p-octyloxyphenyl-5-hexylpyrimidine,
5.5% of 2-p-nonyloxyphenyl-5-hexylpyrimidine,
5.5% of 2-p-decyloxyphenyl-5-hexylpyrimidine and
5.5% of 2-p-dodecyloxyphenyl-5-hexylpyrimidine,
has a melting point of $-12°$ and a clear point of $72°$ and is particularly suitable as a highly multiplexable dielectric.

EXAMPLE B

A liquid crystal phase consisting of
6.6% of 4-ethyl-4'-cyanobiphenyl,
5.4% of 4-propyl-4'-cyanobiphenyl
4.6% of 4-butyl-4'-cyanobiphenyl,
11.4% of trans-1-p-ethylphenyl-4-propylcyclohexane,
6.6% of trans-1-p-ethoxyphenyl-4-propylcyclohexane,
4.6% of 4-cyano-4'-(trans-4-pentylcyclohexyl)-biphenyl
1.4% of 4-ethyl-4'-(trans-4-propylcyclohexyl)-biphenyl,
10.0% of 4-ethyl-2'-fluoro-4'-(trans-4-pentylcyclohexyl)-biphenyl,
5.4% of p-propylphenyl p-trans-4-propylcyclohexylbenzoate,
4.0% of p-propylphenyl p-trans-4-pentylcyclohexylbenzoate,
12.2% of 2-[trans-4-n-hexylcyclohexyl)-phenyl]-5-(trans-4-n-propylcyclohexyl)-pyrimidine
17.8% of 2-(trans-4-n-pentylcyclohexyl)-5-(trans,-trans-4-n-heptylbicyclohex-4'-yl)-pyrimidine,
1.6% of 2-p-hexyloxyphenyl-5-hexylpyrimidine,
1.7% of 2-p-heptyloxyphenyl-5-hexylpyrimidine,
1.7% of 2-p-octyloxyphenyl-5-hexylpyrimidine,
1.7% of 2-p-nonyloxyphenyl-5-hexylpyrimidine,
1.7% of 2-p-decyloxyphenyl-5-hexylpyrimidine and
1.6% of 2-p-dodecyloxyphenyl-5-hexylpyrimidine
is a highly multiplexable dielectric.

EXAMPLE C

A liquid crystal phase consisting of
5.6% of 2-p-hexyloxyphenyl-5-hexylpyrimidine,
5.5% of 2-p-heptyloxyphenyl-5-hexylpyrimidine,
5.6% of 2-p-octyloxyphenyl-5-hexylpyrimidine,
5.6% of 2-p-nonyloxyphenyl-5-hexylpyrimidine,
5.5% of 2-p-decyloxyphenyl-5-hexylpyrimidine,
5.6% of 2-p-dodecyloxyphenyl-5-hexylpyrimidine,
6.6% of 4-ethyl-4'-cyanobiphenyl
5.4% of 4-propyl-4'-cyanobiphenyl,
4.6% of 4-butyl-4'-cyanobiphenyl,
11.4% of trans-1-p-ethylphenyl-4-propylcyclohexane,
6.6% of trans-1-p-ethoxyphenyl-4-propylcyclohexane,
4.6% of 4-cyano-4'-(trans-4-pentylcyclohexyl)-biphenyl,
1.4% of 4-ethyl-4'-(trans-4-propylcyclohexyl)-biphenyl,
10.0% of 4-ethyl-2'-fluoro-4'-(trans-4-pentylcyclohexyl)-biphenyl,
5.4% of p-propylphenyl p-trans-4-propylcyclohexylbenzoate
4.0% of p-propylphenyl p-trans-4-pentylcyclohexylbenzoate
2.0% of 2-[4-(trans-4-n-hexylcyclohexyl)-phenyl]-5-[2-(trans-4-n-propylcyclohexyl)-ethyl]-pyrimidine,
1.7% of 2-[4-(4-trans,trans-n-butylbicyclohex-4'-yl-carbonyloxy)-phenyl]-5-n-butylpyrimidine,
1.1% of 2-[4-(trans-4-n-propylcyclohexylcarbonyloxy)-phenyl]-5-(trans-4-n-heptylcyclohexyl)-pyrimidine
has a viscosity of $29 \times 10^{-3}$ Pa.sec and an optical anisotropy of $+0.16$.

EXAMPLE D

A liquid crystal phase consisting of
7.0% of 2-p-cyanophenyl-5-ethyl-1,3-dioxane,
8.0% of 2-p-cyanophenyl-5-propyl-1,3-dioxane,
8.0% of 2-p-cyanophenyl-5-butyl-1,3-dioxane,
7.0% of 2-p-cyanophenyl-5-pentyl-1,3-dioxane,
9.0% of 4-cyano-4'-(trans-4-pentylcyclohexyl)-biphenyl,
11.0% of 4-ethyl-4'-(trans-4-pentylcyclohexyl)-biphenyl,
7.0% of p-methoxyphenyl trans-4-propylcyclohexanecarboxylate
7.0% of p-ethoxyphenyl trans-4-propylcyclohexanecarboxylate
6.0% of p-methoxyphenyl trans-4-butylcyclohexanecarboxylate
7.5% of 2-[4-trans-4-pentylcyclohexyl)-phenyl]-5(trans-4-propylcyclohexyl)-pyrimidine,
9.5% of 2-[4-trans-4-hexylcyclohexyl)-phenyl]-5-(trans-4-propylcyclohexyl)-pyrimidine,
10.5% of 2-(trans-4-n-pentylcyclohexyl)-5-(trans,-trans-4-heptylbicyclohex-4'-yl)-pyrimidine and
2.5% of 2-[(trans-4-n-pentylcyclohexyl)-5-(trans,-trans-4-propylbicyclohex-4'-yl)-pyrimidine
is a highly multiplexable dielectric.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid crystal phase comprising at least two liquid crystalline components, the improvement wherein at least one component is a compound of the formula $$R^1-(A-Z)_n-A^1-R^2$$

wherein
each of $R^1$ and $R^2$ independently is alkyl of 1–15 C atoms; alkyl of 1–15 C atoms wherein one or two non-adjacent CH$_2$ groups are replaced by O atoms, —O—CO—, —CO—O; and one of $R^1$ and $R^2$ can also be H, CN, F, Cl or Br,
each A independently is 1,4-phenylene (Phe) or 1,4-cyclohexylene (Cy),
each Z independently is —CO—O, —O—CO—, —CH$_2$CH$_2$—, or a single bond, at most two Z's not being a single bond,
$A^1$ is pyrimidine-2,5-diyl,
n is 3 with the proviso that at least one of the groups A is Cy or at least one group Z is not a single bond.

2. A phase of claim 1 wherein said compound is of the formula $R^1-A^1-(A)_p-A^2-R^2$ $R^1-A^1-(A)_{p-1}-A^2-A-R^2$ $R^1-A^1-(A)_{p-2}-A^2-A-A-R^2$ $R^1-A^1-A^2-A-A-R^2$ $R^1-A-A^1-(A)_{p-1}-A^2-R^2$ $R^1-A^2-A^1-(A)_p-R^2$ $R^1-A-A^1-(A)_{p-2}-A^2-A-R^2$ wherein $A^2$ is Cy and p is 2.

3. A phase of claim 1 wherein said compound is of the formula $R^1-A-A^1-A^2-(A)_{p-1}-R^2$ $R^1-A-A-A^1-(A)_{p-2}-A^2-R^2$ $R^1-A-A-A^1-A^2-R^2$ $R^1-A^2-A-A^1-(A)_{p-1}-R^2$ $R^1-A-A^2-A^1-(A)_{p-1}-R^2$ wherein and $A^2$ is Cy and p is 2.

4. A phase of claim 1 wherein said compound is of the formula $R^1-A^1-Z-(A)_{p+1}-R^2$ $R^1-A^1-A-Z-(A)_p-R^2$ $R^1-A^1-A-A-Z-(A)_{p-1}-R^2$ $R^1-A^1-A-A-A-Z-(A)_{p-2}-R^2$ $R^1-A-Z-A^1-(A)_p-R^2$ $R^1-A-A^1-Z-(A)_p-R^2$ $R^1-A-A^1-A-Z-(A)_{p-1}-R^2$ wherein p is 2.

5. A phase of claim 1 wherein said compound is of the formula $R^1-A-A^1-A-A-Z-(A)_{p-2}-R^2$ $R^1-A-Z-A-A^1-(A)_{p-1}-R^2$ $R^1-A-A-Z-A^1-(A)_{p-1}-R^2$ $R^1-A-A-A^1-Z-(A)_{p-1}-R^2$ $R^1-A-A-A^1-A-Z-(A)_{p-2}-R^2$ wherein p is 2.

6. A phase of claim 1 wherein said compound is of the formula $R^1-A-Z-A-Z-(A)_{n-1}-R^2$ $R^1-A-Z-A-A-Z-(A)_{n-2}-R^2$.

7. A phase of claim 1 wherein said compound is of the formula $R^1-A-Z-A-A-A-Z-(A)_{n-3}-R^2$ $R^1-A-A-Z-A-Z-(A)_{n-2}-R^2$ $R^1-A-A-Z-A-A-Z-(A)_{n-3}-R^2$ $R^1-A-Z-A-Z-A-Z-(A)_{n-2}-R^2$ $R^1-A-Z-A-Z-A-A-Z-A-R^2$ $R^1-A-Z-A-Z-A-Z-A-Z-A-R^2$.

8. A phase of claim 1 wherein Z is a single bond.

9. A phase of claim 1 wherein said compound is of the formula $R^1-A^1-A-A^2-A^2-R^2$ $R^1-A^2-A^1-A-A^2-R^2$ $R^1-A^2-A^1-A^2-A^2-R^2$ $R^1-A^1-A-Z-A-A^2-R^2-$ $R^1-A^1-A-Z-A^2-A^2-R^2$ $R^1-A^2-Z-A^1-A-Z-A-R^2$ $R^1-A^2-Z-A^1-A-Z-A^2-R^2$ wherein $A^2$ is Cy.

10. In a liquid crystalline display element comprising a liquid crystalline phase, the improvement wherein the phase is one of claim 1.

11. In an electrooptical display element comprising a liquid crystalline dielectric, the improvement wherein the dielectric is a phase of claim 1.

12. A phase of claim 1 wherein $A^1$ is attached to $R^2$ in its 5-position.

13. A phase of claim 1 wherein said compound is of the formula

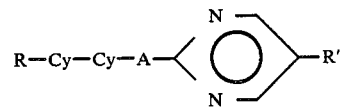

wherein R and R' are each independently alkyl and A is Cy or Phe.

14. A phase of claim 1 wherein in said compound all A's are Cy or Phe and all Z's are a single bond or —CH$_2$CH$_2$—.

15. A phase of claim 14 wherein said compound is of the formula $R-A-A-Z-A-Z-A^1-R'-$ wherein R and R' are each independently alkyl.

* * * * *